United States Patent
Xia et al.

(10) Patent No.: US 8,111,393 B2
(45) Date of Patent: Feb. 7, 2012

(54) STRUCTURE FOR SURFACE ENHANCED RAMAN SPECTROSCOPY

(75) Inventors: Qiangfei Xia, Sunnyvale, CA (US); Jing Tang, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 344 days.

(21) Appl. No.: 12/425,363

(22) Filed: Apr. 16, 2009

(65) Prior Publication Data

US 2010/0265500 A1 Oct. 21, 2010

(51) Int. Cl.
*G01J 3/44* (2006.01)
(52) U.S. Cl. ........................................ 356/301
(58) Field of Classification Search .................. 356/301
See application file for complete search history.

(56) References Cited

U.S. PATENT DOCUMENTS

| 6,899,947 | B2 | 5/2005 | Wei et al. |
| 7,288,419 | B2 * | 10/2007 | Naya ................................ 438/20 |
| 7,692,787 | B2 * | 4/2010 | Fujimaki et al. ............... 356/301 |
| 2004/0180379 | A1 | 9/2004 | Van Duyne et al. |
| 2006/0054506 | A1 | 3/2006 | Natan et al. |
| 2010/0091274 | A1 * | 4/2010 | Bratkovski et al. ........... 356/301 |
| 2010/0253940 | A1 * | 10/2010 | Xia et al. ....................... 356/301 |

OTHER PUBLICATIONS

Vlasov, Y.A. et al. "On-Chip Natural Assembly of Silicon Photonic Bandgap Crystals", Nature, vol. 414, Nov. 15, 2001, pp. 289-293.

* cited by examiner

*Primary Examiner* — Layla Lauchman

(57) ABSTRACT

A structure for surface enhanced Raman spectroscopy is disclosed herein. The structure is made up of a substrate, a self-assembled layer of first metal particles established on the substrate, and a self-assembled layer of second metal particles established such that the second metal particles are positioned at interstitial spaces between the first metal particles. The first metal particles have a first predetermined diameter, and the second metal particles have a second predetermined diameter that is smaller than the first predetermined diameter.

19 Claims, 4 Drawing Sheets

_US 8,111,393 B2_

STRUCTURE FOR SURFACE ENHANCED RAMAN SPECTROSCOPY

BACKGROUND

The present disclosure relates generally to structures for surface enhanced Raman spectroscopy.

Raman spectroscopy is used to study the transitions between molecular energy states when monochromatic light interacts with molecules, which results in the energy of the light photons being shifted, or scattered. The energy shift provides information of the vibrational energy spacing in the molecular system. Surface enhanced Raman spectroscopy (SERS) enhances Raman scattering via molecules adsorbed on, for example, rough metal surfaces or metal nanoparticle aggregates. The Raman signal enhancement is typically related to the large electric fields generated near the metal surface due to localized surface plasmon resonance. However, the SERS signals strongly depend on the excitation light wavelength. To achieve a large Raman enhancement factor, the excitation light wavelength may be tuned in close proximity to the surface plasmon resonance of the rough metal surfaces or metal nanoparticles.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 2A and 2B are schematic top views which together illustrate the formation of an embodiment of a structure including a first metal particle self-assembled layer established on the substrate (FIG. 2A), and a second metal particle self-assembled layer established on the first metal particle self-assembled layer (FIG. 2B), wherein each of the second metal particles is established at an interstitial space between the first metal particles;

FIGS. 2A and 2C are schematic top views which together illustrate the formation of an embodiment of a structure including a first metal particle self-assembled layer established on the substrate (FIG. 2A), and a second metal particle self-assembled layer established on the first metal particle self-assembled layer (FIG. 2C), wherein a plurality of the second metal particles is established at each interstitial space between the first metal particles;

DETAILED DESCRIPTION

Embodiments of the structure disclosed herein advantageously incorporate multiple layers of different sized particles. The inter-particle spacing may be tuned by chemically modifying the surface of one or more of the differently sized particles. The increased particle to particle contact in the structures disclosed herein advantageously creates more "hot spots", or areas/sites at which field enhancement occurs during Raman detection procedures.

As used herein, the term "self-assembled layer" refers to a continuous or discontinuous arrangement of particles that self-align. When a self-assembled layer is established on a substrate surface, the particles are adjacent each other and form a substantially continuous film with interstitial spaces between adjacent particles. When a self-assembled layer is established on another self-assembled layer, the additional self-assembled layer is discontinuous, at least in part because the particles are drawn toward the interstitial spaces within the underlying layer.

Figure 1:
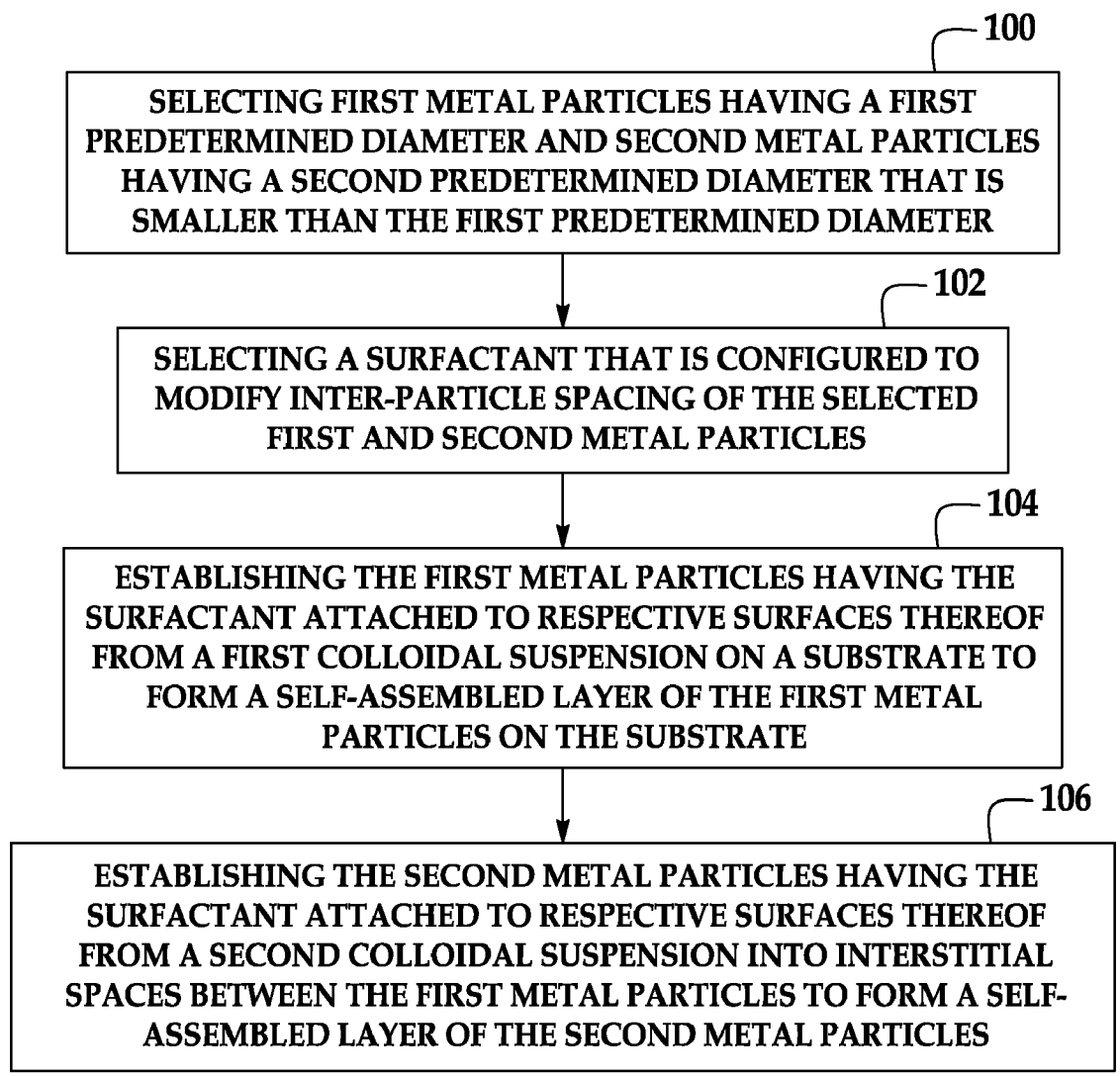
FIG. 1 is a schematic flow diagram illustrating an embodiment of a method for forming an embodiment of a structure.

FIG. 1 depicts an embodiment of the method for forming an embodiment of a structure suitable for use in surface enhanced Raman spectroscopy. It is to be understood that the other Figures will be referenced throughout the discussion of FIG. 1.

The method generally begins by selecting first and second metal particles, as shown at reference numeral 100. The particles may be formed of any noble metal (e.g., gold, silver, etc.), copper, aluminum, or any alloys thereof. Furthermore, the first and second metal particles may be formed of the same metal, or of different metals. It is to be understood that different metal particles will give different plasmonic resonances.

Figure 2:
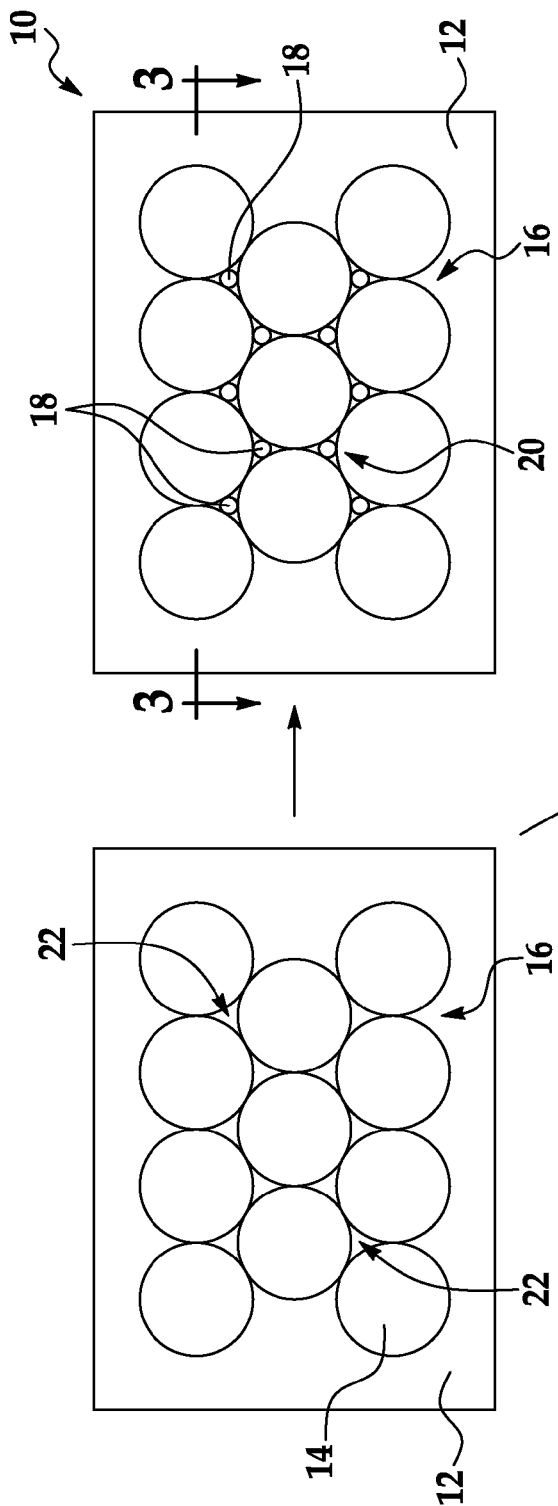
Figure 4:
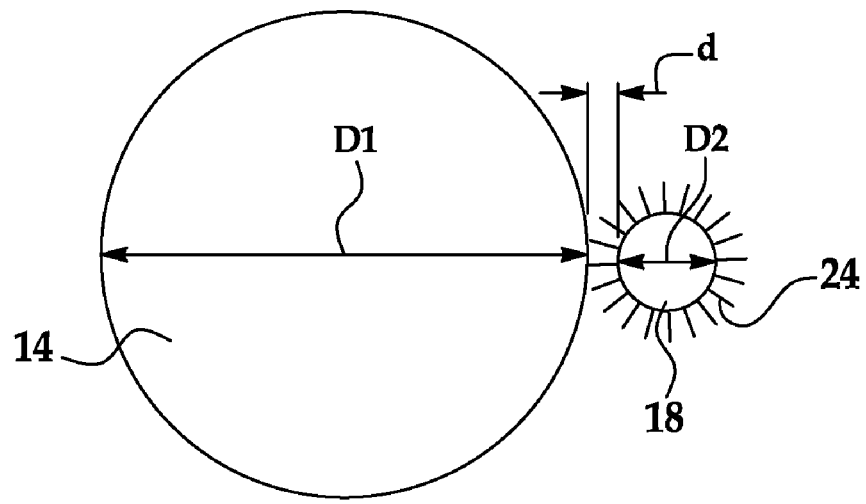
FIG. 4 is a schematic diagram illustrating interaction between one of the first metal particles and one of the second metal particles.

The particles are selected such that the first metal particles have a first predetermined diameter, and the second metal particles have a second predetermined diameter that is different than the first predetermined diameter. Non-limiting examples of the different sized particles 14, 18 established on a substrate 12 are shown in FIGS. 2A, 2B and 2C. Generally, the particles 14 that will form a first self-assembled layer 16 directly on a substrate 12 surface are selected such that their diameter D1 (shown in FIG. 4) is larger than a diameter D2 (also shown in FIG. 4) of the particles 18 that will form a second a self-assembled layer 20 on the first self-assembled layer 16.

Figure 3:
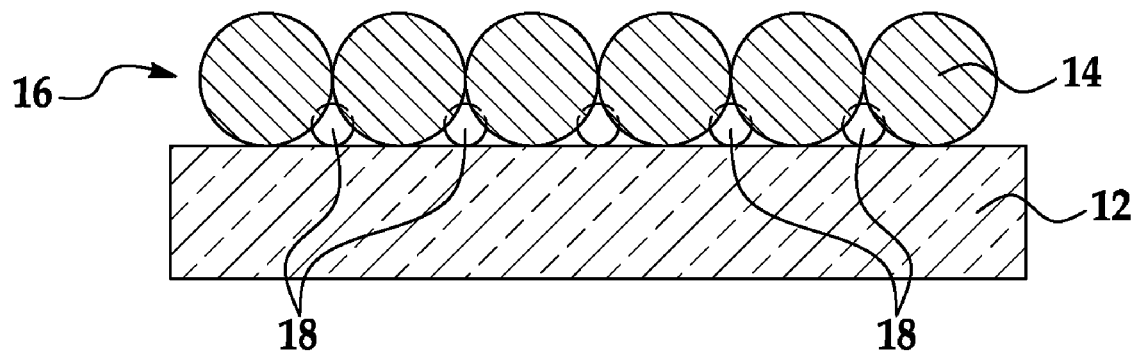
FIG. 3 is a cross-sectional view taken along the 3-3 line of FIG. 2B.

When selecting the particle 14, 18 sizes, it is generally desirable that the second metal particles 18 be of a size (i.e., diameter) that is capable of being positioned (either alone or with one or more other particles 18) at the interstitial spaces 22 (shown in FIG. 2A) between adjacent first particles 14. In one embodiment, the size of the second metal particles 18 is also large enough such that the particles 18 will not be drawn into the spaces 22 between the particles 14 to the point of contacting the surface of the substrate 12. In another embodiment, at least some of the particles are drawn into the spaces 22 between the particles 14 and do contact the surface of the substrate 12 (see, for example, the cross-sectional view taken along the 3-3 line of FIG. 2B shown in FIG. 3). In one embodiment of the structure 10, as shown in FIG. 2B, each smaller particle 18 is positioned at one interstitial space 22. In another embodiment of the structure 10', as shown in FIG. 2C, a plurality of smaller particles 18 is positioned at each interstitial space 22. The number of smaller particles 18 that will be positioned at the interstitial spaces 22 will depend, at least in part, on the particle size ratio (e.g., D1:D2). As such, the ratio of the larger particles 14 to smaller particles 18 may be varied in order to achieve the desirable amount of the smaller particles 18 in the interstitial spaces 22.

In an embodiment, the diameter D1 of the first or larger particles 14 ranges from about 10 nm to about 100 nm, and the diameter D2 of the second or smaller particles 18 ranges from about 1 nm to about 20 nm. In one non-limiting example, the first particles 14 are each 100 nm in diameter D1, and these particles 14 are assembled into a triangular lattice. In this example, the diameter D2 selected for the smaller particles 18 is about 15.5 nm if it is desirable to fill each interstitial space 22 with one particle 18 (e.g., similar to the embodiment shown in FIG. 2B), or is less than 10 nm if it is desirable to position multiple particles 18 at each space 22 (e.g., similar to the embodiment shown in FIG. 2C).

Referring back to FIG. 1, the method also includes selecting a surfactant 24 (schematically shown in FIG. 4) that is configured to modify the inter-particle spacing of the selected first and second metal particles 14, 18. The selected surfactant 24 is used to chemically modify the surface of the smaller particles 18 (shown schematically in FIG. 4) and the larger particles 14. The surfactant selected depends, at least in part, upon the metal selected for the respective particles 14, 18. As such, in some instances, the surfactant 24 coating the particles 14 is different from the surfactant 24 coating the particles 18. Furthermore, the chain length of the surfactant(s) 24 may be selected to alter the distance between adjacent particles 14, between adjacent particles 18, and between adjacent particles 14 and 18 (e.g., the distance d shown in FIG. 4). A surfactant 24 having a longer chain length will increase the distance more than a surfactant 24 having a short chain length. It is believed that smaller distances will provide electromagnetic field enhancement, thereby increasing the hot spots of the device 10, 10' 10".

The surfactant(s) 24 tend to self-assemble on the surface of the particles 14, 18 in solution, thereby forming a monolayer on each of the particles 14, 18. The self-assembling coating process occurs during the synthesis process. The amount of surfactant 24 used will depend, at least in part, upon the number of particles 14, 18, and the size of the particles 14, 18.

Suitable surfactants 24 for the embodiments disclosed herein include thiol based surfactants (e.g., dodecanethiol), carboxylic acids (e.g., oleic acid), or amine based surfactants (e.g., oleylamine). In one non-limiting example, the particles 14, 18 are gold nanoparticles and the surfactant 24 is a thiol based surfactant.

The respective particles 14, 18 and the selected surfactant 24 may be added to an organic solvent to form respective colloidal suspensions of the particles 14, 18. Various organic solvents may be used to form the colloidal suspensions, non-limiting examples of which include toluene, chloroform, hexane, or other organic solvents.

In addition to the advantages set forth above, the surfactant 24 may also advantageously stabilize the particles 14 and/or 18 in the selected organic solvent. More specifically, the selected surfactant 24 advantageously keeps the respective particles 14, 18 in a mono-dispersed state within the colloidal suspension.

As shown at reference numeral 104 in FIG. 1, the method continues with the first metal particles 18 (which may have the surfactant 24 attached to respective surfaces thereof) being established from a first colloidal suspension onto a substrate 12 to form a self-assembled layer 16 of the first metal particles 14.

Figure 5:
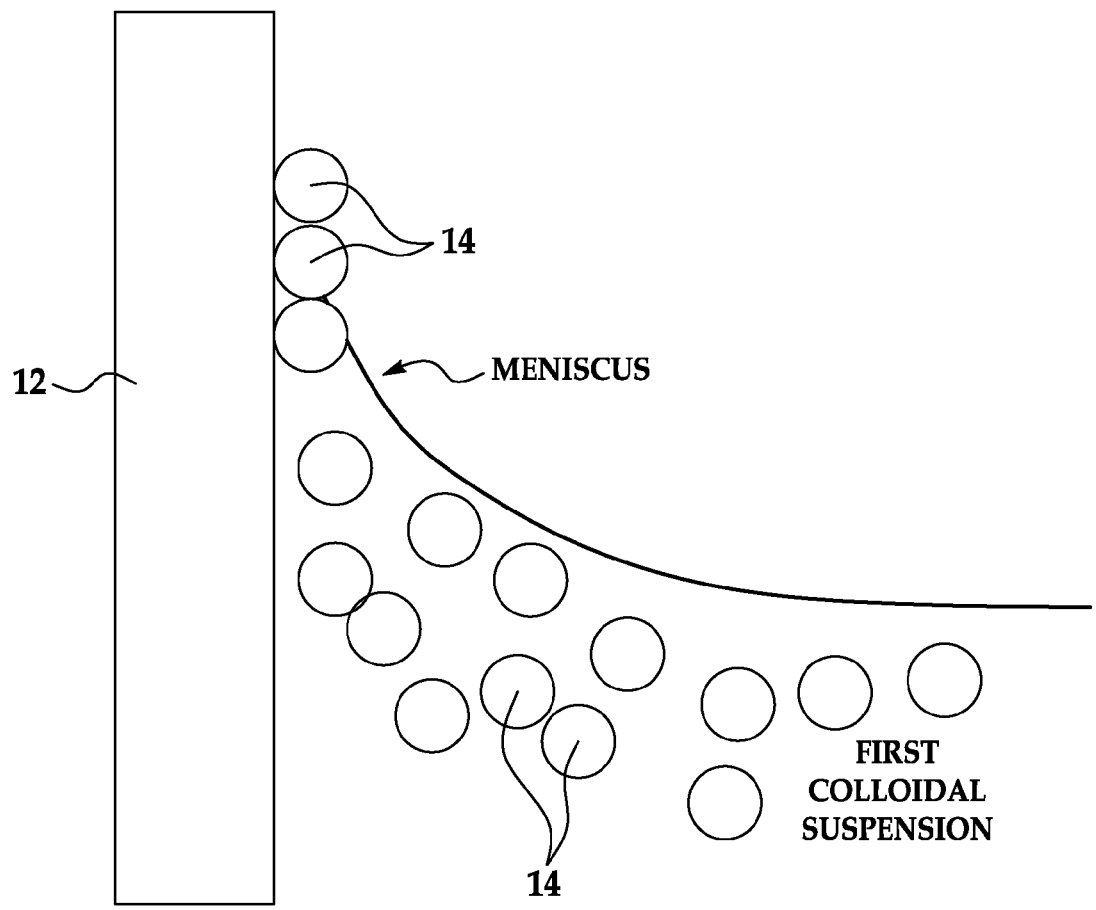
FIG. 5 is a schematic diagram illustrating an approach for establishing each of the self-assembled layer of the first metal particles and the self-assembled layer of the second metal particles.

A non-limiting example of this process is shown in FIG. 5. Self-assembling processes that may be used to form the layer 16 (and also the layer 20) include a Langmuir-Blodgett technique, spin casting, or drop casting. FIG. 5 schematically illustrates the Langmuir-Blodgett technique. As depicted, the particles 14 are deposited from the surface of the first colloidal suspension onto the surface of the substrate 12 by immersing the solid substrate 12 into the colloidal suspension. A monolayer of the particles 14 is adsorbed homogeneously with (or from) the immersion, and thus the layer 16 having a very accurate thickness is formed.

This process is repeated, or another process (e.g., spin or drop casting) is performed, using the second colloidal suspension (not shown) including the second metal particles 14, which may have the surfactant 24 attached to respective surfaces thereof. As such, the second self-assembled layer 20 of second particles 18 is formed at the interstitial spaces 22 between the particles 14 of the first self-assembled layer 16 (as shown in FIGS. 2B and 2C), as shown at reference numeral 106 of FIG. 1. It is to be understood that during deposition of the second metal particles 18, capillary forces draw the second metal particles 18 into the interstitial spaces 22 between the first particles 14. As depicted in FIGS. 2B and 2C, due at least in part to the capillary action on the particles 18, the second self-assembled layer 20 is a discontinuous layer.

It is to be understood that the substrate 12 may be any suitable substrate. In an embodiment, the substrate 12 is selected such that it does not interfere with the plasmonic resonance of the particles 14, 18. Non-limiting examples of suitable substrate materials include insulators (e.g., glass, quartz, ceramic (alumina), etc.), polymeric material(s) (e.g., polycarbonate, polyamide, acrylics, etc.), or semiconductors (e.g., silicon, InP, GaAs, InAs, $Ga_xAl_{1-x}As$ (where $0<x<1$), $In_xGa_{1-x}As_yP_{1-y}$ (where $0<x<1$, $0<y<1$)), silicon-on-insulator (SOI) substrates, or group III-V semiconductors established on silicon or SOI substrates.

The method disclosed herein may be suitable for a larger or smaller substrate wafer. In one embodiment, the substrate 12 may be a wafer having a diameter, length and/or width ranging from about 1 cm to about 5 in. In one embodiment, the wafer length is 4 inches or less. The substrate 12 size may be selected, at least in part, based upon the end application, the cost involved, etc. As such, the example sizes given herein are for illustrative purposes, and it is to be understood that any desirable substrate size may be utilized.

When metallic particles 14, 18 are dispersed in organic solvents, an untreated substrate surface is generally suitable for achieving the desired self-assembled layers 16, 20. However, in some instances, the substrate may also be functionalized prior to establishing the layers 16, 20 thereon. Such functionalization may be particularly desirable in order to enhance the adhesion between the substrate 12 and the particles 14. When attaching the particles 14 onto substrate 12, bifunctional linker molecules may be used for the functionalization of the substrate surface. Suitable bifunctional linker molecules are in the general form of X—R—Y, where X and Y are each independently selected from $NH_2$, SH, COOH, and $Si(OR)_3$, and R represents an alkyl or aryl. As one non-limiting example, for modifying a silicon or glass substrate, a silane (e.g., 3-aminopropyltrimethoxysilane (APTMS)) may be used. As another non-limiting example, for modifying metallic surfaces such as Ag or Au, $SH(CH_2)_nSH$ or $SH(CH_2)_nNH_2$ (where, in either example, n varies from 6 to 18) may be used (e.g., 1,6-hexanedithiol). Still other non-limiting examples of suitable linker molecules are mercaptopropionic acid and 4,4'-Diaminoazobenzene.

In one embodiment of the method, the surfactant 24 is removed after the self-assembled layers 16, 20 are formed. It is believed that the removal of the surfactant 24 after the layers 16, 20 are formed will not deleteriously affect the inter-particle spacing. In an embodiment, the surfactant 24 is removed via plasma etching.

Figure 6:
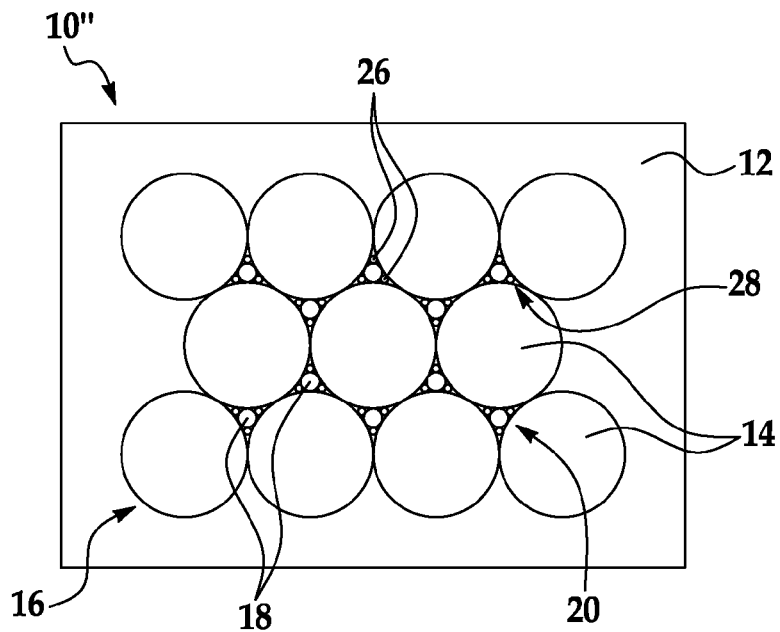
FIG. 6 is a top view of an embodiment of a structure including first, second, and third self-assembled layers.

Embodiments of the method of FIG. 1 may also include the additional step of forming still another self-assembled layer 28 on the first and second self-assembled layers 16, 20. This embodiment of the structure 10" is shown in FIG. 6. In forming this structure 10", an additional colloidal suspension of third particles 26 (which have an even smaller diameter than the diameter D2 of the second metal particles 18) is formed. The method(s) previously described are used to form the third self-assembled layer 28. It is to be understood that these particles 26 self-assemble into the interstitial spaces between the first particles 14 and the second particles 18.

Embodiments of the structure 10, 10', 10" disclosed herein are suitable for use in standard Raman detection procedures. Generally, analyte molecules are distributed on the particles, and are subsequently subjected to laser excitation of suitable wavelengths. The resulting signals are detected using known detectors. As previously mentioned, the field is enhanced due, at least in part, to the increased particle 14, 18, 26 to particle 26, 18, 14 contact.

While several embodiments have been described in detail, it will be apparent to those skilled in the art that the disclosed embodiments may be modified. Therefore, the foregoing description is to be considered exemplary rather than limiting.

What is claimed is:

1. A structure for surface enhanced Raman spectroscopy, comprising:
   a substrate;
   a self-assembled layer of first metal particles established on the substrate, the first metal particles having a first predetermined diameter; and
   a self-assembled layer of second metal particles established such that one or more of the second metal particles are positioned at interstitial spaces between the first metal particles and do not contact a surface of the substrate, the second metal particles having a second predetermined diameter that is smaller than the first predetermined diameter.

2. The structure as defined in claim 1 wherein each of the second metal particles is positioned in a respective interstitial space between adjacent first metal particles.

3. The structure as defined in claim 2 wherein the positioning of the second metal particles in relation to the first metal particles increases a number of field enhancement sites for the structure.

4. The structure as defined in claim 1 wherein a respective plurality of the second metal particles is positioned in each interstitial space between adjacent first metal particles.

5. A structure for surface enhanced Raman spectroscopy, comprising:
   a substrate;
   a self-assembled layer of first metal particles established on the substrate, the first metal particles having a first predetermined diameter;
   a self-assembled layer of second metal particles established such that one or more of the second metal particles are positioned at interstitial spaces between the first metal particles, the second metal particles having a second predetermined diameter that is smaller than the first predetermined diameter; and
   a surfactant present on a surface of at least some of the first metal particles and at least some of the second metal particles.

6. The structure as defined in claim 5 wherein the surfactant is selected from thiol based surfactants, carboxylic acids, and amine based surfactants.

7. The structure as defined in claim 6 wherein the first and second metal particles are selected from noble metals, copper, aluminum, and alloys thereof.

8. The structure as defined in claim 7 wherein the first and second metal particles are gold, and wherein the surfactant is a thiol based surfactant.

9. The structure as defined in claim 1 wherein the first predetermined diameter ranges from about 10 nm to about 100 nm, and wherein the second predetermined diameter ranges from about 1 nm to about 20 nm.

10. A structure for surface enhanced Raman spectroscopy, comprising:
    a substrate;
    a self-assembled layer of first metal particles established on the substrate, the first metal particles having a first predetermined diameter;
    a self-assembled layer of second metal particles established such that one or more of the second metal particles are positioned at interstitial spaces between the first metal particles, the second metal particles having a second predetermined diameter that is smaller than the first predetermined diameter; and
    a self-assembled layer of third metal particles established at interstitial spaces between the first metal particles and the second metal particles, the third metal particles having a third predetermined diameter that is smaller than the second predetermined diameter.

11. A method for making a structure for surface enhanced Raman spectroscopy, the method comprising:
    selecting first metal particles having a first predetermined diameter and second metal particles having a second predetermined diameter that is smaller than the first predetermined diameter;
    selecting a surfactant that is configured to modify interparticle spacing of the selected first and second metal particles;
    establishing the first metal particles having the surfactant attached to respective surfaces thereof from a first colloidal suspension on a substrate to form a self-assembled layer of the first metal particles on the substrate; and
    establishing the second metal particles having the surfactant attached to respective surfaces thereof from a second colloidal suspension into interstitial spaces between the first metal particles to form a self-assembled layer of the second metal particles.

12. The method as defined in claim 11, further comprising functionalizing a surface of the substrate prior to establishing the colloidal suspension of the first metal particles having the surfactant attached to respective surfaces thereof.

13. The method as defined in claim 11 wherein capillary forces draw the second metal particles into the interstitial spaces between adjacent first metal particles during the establishing of the colloidal suspension of the second metal particles having the surfactant attached to respective surfaces thereof.

14. The method as defined in claim 13, further comprising selecting the first metal particles and the second metal particles such that each of the second metal particles is configured to be drawn into a respective interstitial space between adjacent first metal particles.

15. The method as defined in claim 13, further comprising selecting the first metal particles and the second metal particles such that a respective plurality of the second metal particles is configured to be drawn into each interstitial space between adjacent first metal particles.

16. The method as defined in claim 11 wherein the establishing steps are accomplished via at least one of a Langmuir-Blodgett technique, spin casting, or drop casting.

17. The method as defined in claim 11, further comprising removing the surfactant from the first and second metal particles.

18. The method as defined in claim 11 wherein each of the first metal particles selected has the first predetermined diameter ranging from about 10 nm to about 100 nm, and wherein each of the second metal particles selected has the second predetermined diameter ranging from about 1 nm to about 20 nm.

19. The method as defined in claim 11, further comprising:

selecting third metal particles having a diameter smaller than the diameter of the second metal particles; and establishing the third metal particles having the surfactant attached to respective surfaces thereof from a colloidal suspension into interstitial spaces between the first metal particles and the second metal particles to form a self-assembled layer of the third metal particles.

\* \* \* \* \*